US00PP27435P2

(12) United States Plant Patent
Spruyt

(10) Patent No.: US PP27,435 P2
(45) Date of Patent: Nov. 29, 2016

(54) ***PENNISETUM* PLANT NAMED 'JS JOMMENIK'**

(50) Latin Name: *Pennisetum alopecuroides*
Varietal Denomination: JS Jommenik

(71) Applicant: Spruyt Select GCV, Buggenhout (BE)

(72) Inventor: Jan Spruyt, Lebbeke (BE)

(73) Assignee: Spruyt Select GCV, Buggenhout (BE)

( * ) Notice: Subject to any disclaimer, the term of this patent is extended or adjusted under 35 U.S.C. 154(b) by 0 days.

(21) Appl. No.: 14/757,284

(22) Filed: Dec. 11, 2015

(51) Int. Cl.
*A01H 5/12* (2006.01)

(52) U.S. Cl.
USPC ..... Plt./465

(58) Field of Classification Search
USPC ..... Plt./465
See application file for complete search history.

(56) References Cited

PUBLICATIONS

PLUTO Plant Variety Database Aug. 2, 2016.p. 1.*

* cited by examiner

*Primary Examiner* — Annette Para
(74) *Attorney, Agent, or Firm* — Barbara Campbell; Bethany R. Roahrig; Cochran Freund & Young LLC

(57) ABSTRACT

A new *Pennisetum* plant particularly distinguished by having a compact growth habit, green-yellow to yellow foliage, and a bushy, semi-globular plant shape, is disclosed.

1 Drawing Sheet

Genus and species: *Pennisetum alopecuroides.*
Variety denomination: 'JS Jommenik'.

BACKGROUND OF THE NEW PLANT

The present invention comprises a new and distinct variety of *Pennisetum*, botanically known as *Pennisetum alopecuroides* and hereinafter referred to by the variety name 'JS Jommenik'. 'JS Jommenik' was discovered as a branch (shoot) mutation in *Pennisetum alopecuroides* 'Gelbstiel' (unpatented) in summer 2007 in the nursery of the inventor in Buggenhout, Belgium.

'JS Jommenik' was first propagated through division in summer 2009 in summer 2007 in the nursery of the inventor in Buggenhout, Belgium. 'JS Jommenik' was found to reproduce true to type in successive generations of asexual propagation via tissue culture and division in Buggenhout, Belgium.

CROSS REFERENCE TO RELATED APPLICATIONS

A Community Plant Variety Rights application has been filed with the Community Plant Variety Office on Sep. 9, 2014, File No. 2014/2194.

SUMMARY

The following are the most outstanding and distinguishing characteristics of this new variety when grown under normal horticultural practices in Buggenhout, Belgium.

1. A compact growth habit;
2. Green-yellow to yellow foliage; and
3. A bushy, semi-globular plant shape.

DESCRIPTION OF THE PHOTOGRAPHS

This new *Pennisetum* plant is illustrated by the accompanying photographs which show a whole plant view and a close-up view of the foliage. The photographs are of a plant approximately two-years-old grown outdoors in Buggenhout, Belgium. The colors shown are as true as can be reasonably obtained by conventional photographic procedures.

DESCRIPTION OF THE NEW VARIETY

Figure 1:
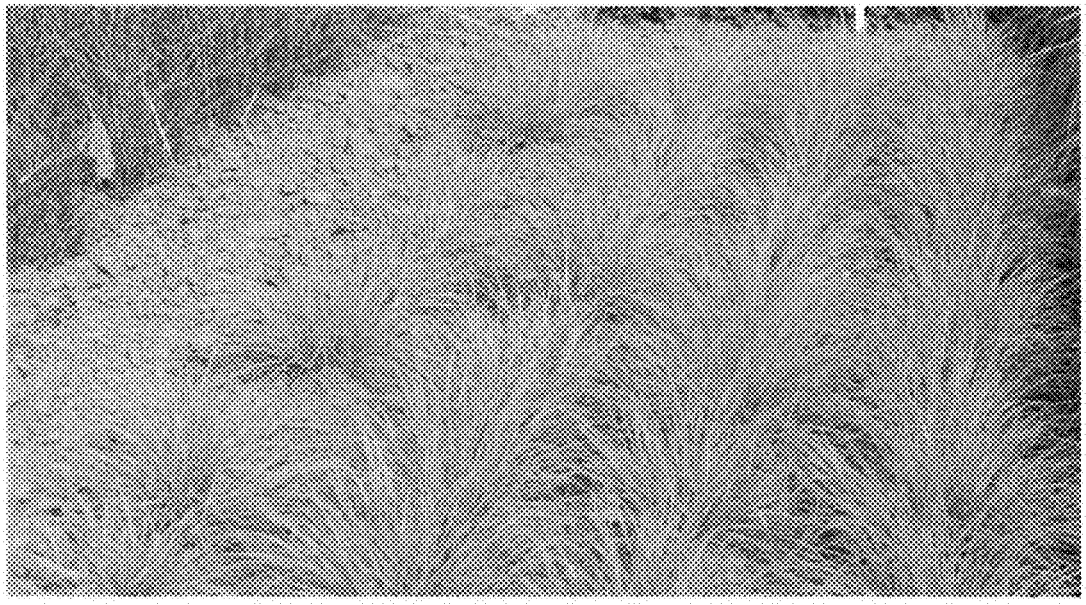
FIG. 1 shows an overall view of multiple plants in rows grown outside.
Figure 2:
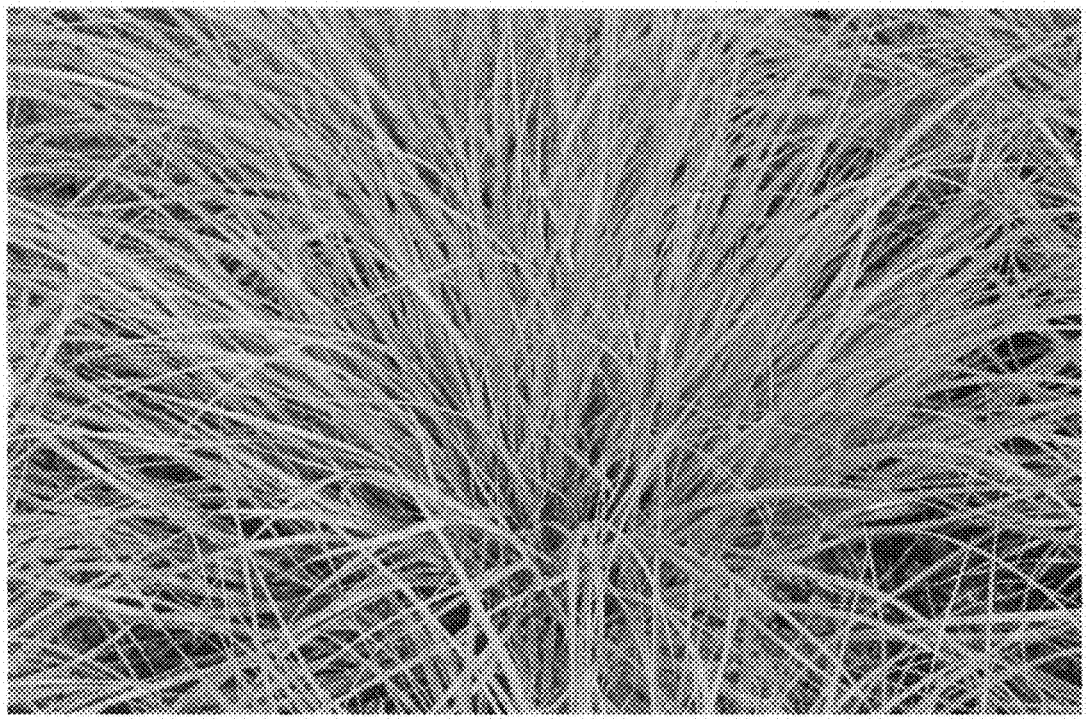
FIG. 2 shows a close-up of the foliage of the plant.

The following detailed descriptions set forth the distinctive characteristics of 'JS Jommenik'. The data which define these characteristics were collected from asexual reproductions carried out in Buggenhout, Belgium. Data was collected on two-year-old plants in November 2015. Observations were taken indoor, and next to a north-facing clear-glass window where the average day temperatures were approximately 7° C. to 18° C. and where the average night temperatures were approximately −1° C. to 12° C. Color references are to The R.H.S. Colour Chart of The Royal Horticultural Society of London (R.H.S.), 6$^{th}$ edition (2015).

Classification:

*Family.*—Poaceae.
*Species.*—*Pennisetum alopecuroides.*
*Variety.*—'JS Jommenik'.

Plant:

*Type.*—Herbaceous perennial (grass).
*Time to produce a finished plant.*—Approximately 26 weeks from propagation to a saleable plant.
*Appropriate container size and/or cropping system.*—Field-grown, in 13 cm pots and larger.
*Plant shape.*—Globular.
*Growth habit.*—Basal leafy shoots.

*Plant height*.—Soil level to top of foliar plane: Average is 33.0 cm. Soil level to top of floral plane: Not applicable; no flowers observed to date.

*Plant diameter or area of spread*.—Average is 44.5 cm.

*Growth rate*.—Low.

*Plant vigor*.—Low.

*Branching habit*.—Leaves in basal leafy shoots, no main branches or lateral branches present.

*Pinching required*.—No.

*High temperature tolerance*.—Unknown, at least tolerant to temperatures up to 35 degrees C.

*Low temperature tolerance*.—Unknown, at least hardy to USDA zone 6.

*USDA hardiness zones*.—USDA zone 6 to zone 9.

*Tolerance to rain*.—High.

*Tolerance to wind*.—High.

Foliage:

*Leaf arrangement*.—Alternate, growing in basal leafy shoots.

*Type*.—Single and unlobed.

*Number of leaves per rosette*.—Average is 6.

*Shape*.—Linear.

*Aspect*.—Carinate.

*Apex*.—Narrow acuminate.

*Margin*.—Entire, very sparsely pubescent.

*Base*.—Sheathing.

*Sheath length*.—Average is 5.8 cm.

*Sheath width*.—Average is 0.2 cm.

*Sheath color*.—RHS 144A (Yellow-green) and fading lighter towards the base, RHS 144D.

*Length*.—Average is 23.0 cm.

*Width*.—Average is 0.4 cm.

*Texture* (*both upper and lower surfaces*).—Very sparsely pubescent with soft thin hairs, average length is 0.2 cm, colored RHS 156D (Greyed-white).

*Rugosity*.—Both upper and lower surfaces are non-rugose.

*Luster* (*both upper and lower surfaces*).—Very slightly glossy.

*Color, immature leaf*.—Upper surface: RHS 154A (Yellow-green) to RHS 1A (Green-yellow) and fading to RHS 144A (Yellow-green) towards the base. Lower surface: RHS 154A (Yellow-green) and fading to RHS 144A (Yellow-green towards the base.

*Color, mature leaf*.—Upper surface: RHS 154A (Yellow-green) to RHS 1A (Green-yellow) and fading to RHS 144A (Yellow-green) towards the base. Lower surface: Lower surface: RHS 154A (Yellow-green) and fading to RHS 144A (Yellow-green) towards the base.

*Venation pattern*.—Parallel.

*Mature leaf venation color*.—Upper surface: RHS 154A (Yellow-green) to RHS 1A (Green-yellow) and fading to RHS 144A (Yellow-green) towards the base. Lower surface: Lower surface: RHS 154A (Yellow-green) and fading to RHS 144A (Yellow-green) towards the base.

*Mature leaf color in autumn fading to, both upper lower surfaces*.—Between RHS 20A and RHS 20B (Yellow-orange); in between 20A and 20B.

*Petioles*.—Absent.

Flowers: None observed.

Reproductive organs: None observed.

Fruit and seed set: None observed.

Disease and pest resistance: Similar to other *Pennisetum* varieties.

COMPARISON WITH PARENTAL LINE AND KNOWN VARIETY

'JS Jommenik' is distinguished from its parents as described in Table 1.

TABLE 1

| Characteristic | 'JS Jommenik' | Mutation parent 'Gelbstiel' |
|---|---|---|
| Foliage color | Green-yellow to yellow | Green |
| Plant height | Average is 35 cm | Average is 60 cm |

'JS Jommenik' can be compared to the commercial *Pennisetum* plant variety 'Piglet' (U.S. Plant Pat. No. 19,074). Differences between the two varieties are described in Table 2.

TABLE 2

| Characteristic | 'JS Jommenik' | 'Piglet' |
|---|---|---|
| Foliage color | Green-yellow to yellow | Green |

I claim:

1. A new and distinct variety of *Pennisetum* plant named 'JS Jommenik' as illustrated and described herein.

* * * * *